(12) United States Patent
Graves et al.

(10) Patent No.: US 11,330,061 B2
(45) Date of Patent: May 10, 2022

(54) REMOTE DEVICE MONITORING DEVICE AND SYSTEM

(71) Applicant: Parasitics LLC, Torrance, CA (US)

(72) Inventors: Daniel Graves, Torrance, CA (US); Andrew Gifft, Redondo Beach, CA (US)

(73) Assignee: Parasitics LLC, Torrance, CA (US)

( * ) Notice: Subject to any disclaimer, the term of this patent is extended or adjusted under 35 U.S.C. 154(b) by 128 days.

(21) Appl. No.: 16/965,275

(22) PCT Filed: Feb. 27, 2019

(86) PCT No.: PCT/US2019/019892
§ 371 (c)(1),
(2) Date: Jul. 27, 2020

(87) PCT Pub. No.: WO2019/169032
PCT Pub. Date: Sep. 6, 2019

(65) Prior Publication Data
US 2021/0075862 A1 Mar. 11, 2021

Related U.S. Application Data

(60) Provisional application No. 62/636,956, filed on Mar. 1, 2018.

(51) Int. Cl.
*G06F 15/173* (2006.01)
*H04L 67/125* (2022.01)
(Continued)

(52) U.S. Cl.
CPC .......... *H04L 67/125* (2013.01); *G06F 1/3209* (2013.01); *G16H 40/67* (2018.01); *H04W 76/10* (2018.02); *G06F 1/3218* (2013.01)

(58) Field of Classification Search
None
See application file for complete search history.

(56) References Cited

U.S. PATENT DOCUMENTS 7,138,914 B2   11/2006   Culpepper et al.

OTHER PUBLICATIONS

BlueCalypso Webite Demonstration, URL https://portal.bluecalypso.com, Sep. 19, 2016.
(Continued)

*Primary Examiner* — Brian Whipple
*Assistant Examiner* — Gregory P Tolchinsky

(57) ABSTRACT

A remote monitoring device is provided for monitoring the status of an electronic display unit. The remote monitoring device includes a current detector connected to an input power cord that provides power to said electronic display unit, the current detector outputting a current detection signal based on the current of the input power cord. The remote monitoring device further includes a cellular communication module that communicates via a cellular communication network to an internet-connected server, and a Wi-Fi communication module that communicates with one or more local Wi-Fi access points and obtains access point identification information related to the one or more local Wi-Fi access points. The remote monitoring device also includes a memory module that stores data and instructions, and a processor unit in communication with the current detector, the cellular communication module, the Wi-Fi communication module and the memory module, the processor unit executing the instructions to (1) periodically record an electric current value associated with the current detection signal, (2) generate a message containing the recorded electric current values and the access point identification information, (3) provide the message to the cellular communication module, and (4) instruct the cellular com-
(Continued)

munication module to send the message via the cellular communication network to the internet-connected server.

16 Claims, 13 Drawing Sheets

(51) Int. Cl.
*G16H 40/67* (2018.01)
*H04W 76/10* (2018.01)
*G06F 1/3209* (2019.01)
*G06F 1/3218* (2019.01)

(56) References Cited

OTHER PUBLICATIONS

BlueCalypso website home page, URL https://web.archive.org/web/20171220160437/http://bluecalypso.com/, Dec. 20, 2017.
BlueCalypso website KioSentrix page, URL https://web.archive.org/web/20171214192123/http://bluecalypso.com/kiosentrix/, Dec. 14, 2017.
BlueCalypso website PopTrak page, URL https://web.archive.org/web/20180217190631/http://bluecalypso.com/poptrakl, Feb. 17, 2018.
Shelfbucks website home page, URL https://web.archive.org/web/20171215044419/http://www.shelfbucks.com/, Dec. 15, 2017.
Shelfbucks website Insights page, URL https://web.archive.org/web/20171218035132/http://www.shelfbucks.com/insights-video-library-for-2016-website-0, Dec. 18, 2017.
Shelfbucks website Collect Data page, URL, https://web.archive.org/web/20170518033224/http://www.shelfbucks.com/george-garrick-collect-data-by-individual-display-individual-store-video?_hstc=42324218.224147d3911c45611eed557246c86c25.1481574698229.1481746447426.1481817550206.3&_hssc=42324218.1.1481821641071&_hsfp=1094832644&hsCtaTracking=b2e90f40-8d56-4fad-a78d-ea296f54d6fd%7C2e46168f-1723-43c4-bac2-7c6fcffb4189 , May 18, 2017.
Shelfbucks website How It Works page, URL https://web.archive.org/web/20170505091613/http://www.shelfbucks.com/charlie-walden-how-it-works?_hstc=42324218.224147d3911c45611eed557246c86c25.1481574698229.1481746447426.1481817550206.3&_hssc=42324218.1.1481821641071&_hsfp=1094832644&hsCtaTracking=7e25d068-259f-404b-8f63-b4d1ad8ec0aa%7C2b2881af-a7b7-4dc0-9a56-15cea112d2b3, May 5, 2017.
Shelfbucks website What Can Be Measured page, URL https://web.archive.org/web/20171220054314/http://www.shelfbucks.com/what-can-be-measured-cam-be-improved-video-2016-kevin-staumbaugh?_hstc=42324218.224147d3911c45611eed557246c86c25.1481574698229.1481746447426.1481817550206.3&_hssc=42324218.1.1481821641071&_hsfp=1094832644&hsCtaTracking=2ea240f8-553b-4f5d-932c-099a79355312%7Cd7c7d4ec-ca09-4e17-abef-52b77e8ecf60, Dec. 20, 2017.
Shelfbucks website Smart Displays page, URL https://web.archive.org/web/20170514212956/http://www.shelfbucks.com/we-make-displays-smart-video-2016-kris-milam?_hstc=42324218.224147d3911c45611eed557246c86c25.1481574698229.1481746447426.1481817550206.3&_hssc=42324218.1.1481821641071&_hsfp=1094832644&hsCtaTracking=587242d7-d620-4df2-82a6-d4bdc48d63a7%7C38b39902-ced8-4fb5-af73-1e9e8c5d82c2, May 14, 2017.

REMOTE DEVICE MONITORING DEVICE AND SYSTEM

CROSS REFERENCE TO RELATED APPLICATIONS

This application is a Section 371 U.S. national stage application of PCT Application No. PCT/US2019/019892, filed on Feb. 27, 2019, entitled "REMOTE DEVICE MONITORING DEVICE AND SYSTEM," and claims priority to U.S. Provisional Application No. 62/636,956, filed on Mar. 1, 2018, entitled "REMOTE DEVICE MONITORING DEVICE AND SYSTEM," all of which are incorporated by reference herein.

BACKGROUND OF THE INVENTION

1. Field of Invention

The present invention relates to a parasitic monitoring system comprising a monitoring device that detects the electric current status of a nearby electric device or machine, and sends information related to the electric current status to a remote internet accessible server via a wireless data communication network, whereupon the remote server analyzes the electric current status information related to the electric device and determines device usage and events related to the electric device.

2. Description of Related Art

Various types of electric devices and machines are frequently placed in, or distributed to, different places of business and commerce settings for operation in those settings. The owners of such electric devices and machines are often not the owners and proprietors of the business and commerce settings into which the electric devices are placed. For example, electronic display devices for displaying products of a particular brand are provided for placement into retail stores on behalf of the company that produces that brand of products. Such display devices may include audio and/or video playback devices for playing recorded audio/video information about the particular brand of products associated with the display device, and also may include input buttons and sensors for customer interaction and detection.

Numerous ones of these same electronic display devices may be provided to various stores and business in a local, regional, nationwide and even global context on behalf of a particular product company. Unfortunately, the company, or marketing agency working on its behalf, does not necessarily have any visibility into how and when the electronic display devices are actually placed into the particular stores and businesses and made operational to be viewed by and/or interact with the customers of those stores and businesses. Even when an electronic display device is placed out on the floor of a store and made operational, the marketing company or other agency acting on behalf of the product company does not have insight into how often a customer interacts with the electronic display device. As an example, for electronic display devices that include a video playback device such as a monitor for playing back digital video content related to a brand product, the company or agency associated with the brand product does not have knowledge of how often the video content is played by passing customers or how long the video content is viewed. Such information would be valuable to the product company in determining if the electronic display device is being effectively utilized by the various stores and businesses to which it is provided, and if so, whether customers show interest in viewing and interacting with the electronic display device.

Of course, the above example of electronic display devices is just one possible example of various types of electric devices and machines that are provided to, or placed into, various different settings by owners or stakeholders who are keenly interested in whether such devices and machines are ever actually setup and made operational, but also whether such devices and machines are being effectively utilized for their intended purpose. Other examples of such devices and machines include, but are not limited to, vending machines, health care monitoring or dispensing machines, information kiosks, etc. In all of these examples, the common problem is that the devices/machines are remotely placed into various settings from the company or agency which provides the devices/machines to the various settings, and therefore the company or agency does not have accurate and direct insight into how the devices/machines are being utilized.

Even if such devices/machines had the capability to store usage information locally in a memory or a recording device provided in the device/machine, someone would need to travel to the store or business setting where the device/machine is located to obtain that usage information. Given that there are often thousands of the same device/machine associated located in stores and businesses nationwide, and often globally, the effort to obtain the usage information associated with each particular device/machine across the nation in a timely manner would be oppressively burdensome and inefficient. Many existing device/machines, such as electronic display devices, do not have the capability to track and store usage information. Furthermore, the cost and complexity of implementing such usage information tracking and storage capability into the devices/machines can be prohibitive for the companies that provide the devices/machines to the various stores and businesses.

SUMMARY OF THE INVENTION

In an aspect, a remote monitoring device is provided for monitoring the status of an electronic display unit. The remote monitoring device includes a current detector connected to an input power cord that provides power to said electronic display unit, the current detector outputting a current detection signal based on the current of the input power cord. The remote monitoring device further includes a cellular communication module that communicates via a cellular communication network to an internet-connected server, and a Wi-Fi communication module that communicates with one or more local Wi-Fi access points and obtains access point identification information related to the one or more local Wi-Fi access points. The remote monitoring device also includes a memory module that stores data and instructions, and a processor unit in communication with the current detector, the cellular communication module, the Wi-Fi communication module and the memory module, the processor unit executing the instructions to (1) periodically record an electric current value associated with the current detection signal, (2) generate a message containing the recorded electric current values and the access point identification information, (3) provide the message to the cellular communication module, and (4) instruct the cellular communication module to send the message via the cellular communication network to the internet-connected server.

In another aspect, a method is provided for monitoring the status of an electronic display unit by monitoring an input power cord that provides power to the electronic display unit and outputting a current detection signal based on the current of the input power cord, obtaining access point identification information related to one or more local Wi-Fi access points detected by a Wi-Fi communication module, recording, on a frequent basis, an electric current value associated with the current detection signal, generating a message containing the recorded electric current values and the access point identification information, and providing the message to a cellular communication module and instructing the cellular communication module to send the message via a cellular communication network to an internet-connected server.

In an aspect, an internet-connected server is provided for monitoring the status of an electronic display unit, the internet-connected server comprising an internet communication module that communicates with the internet, a memory module that stores data and instructions, and a processor unit in communication with the internet communication module and the memory module, the processor unit executing the instructions to (1) receive a message from a remote monitoring device via the internet communication module, the message containing electric current values of an electronic display unit and access point identification information associated with the remote monitoring device, (3) determine the location of the remote monitoring device and electronic display unit based on the access point identification information, (4) compare electric current values contained in received message with at least one electric current threshold to determine whether a usage event has occurred at the electronic display unit, and (5) store the location and any determined events associated with the electronic display unit.

In another aspect, a method is provided for monitoring the status of an electronic display unit by receiving a message from a remote monitoring device via an internet communication module, the message containing electric current values of an electronic display unit and access point identification information associated with the remote monitoring device, determining the location of the remote monitoring device and electronic display unit based on the access point identification information, comparing the electric current values contained in the received message with at least one electric current threshold to determine whether a usage event has occurred at the electronic display unit, and storing the location and any determined usage events associated with the electronic display unit.

The foregoing, and other features and advantages of the invention, will be apparent from the following, more particular description of exemplary aspects of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

DETAILED DESCRIPTION

Figure 1:
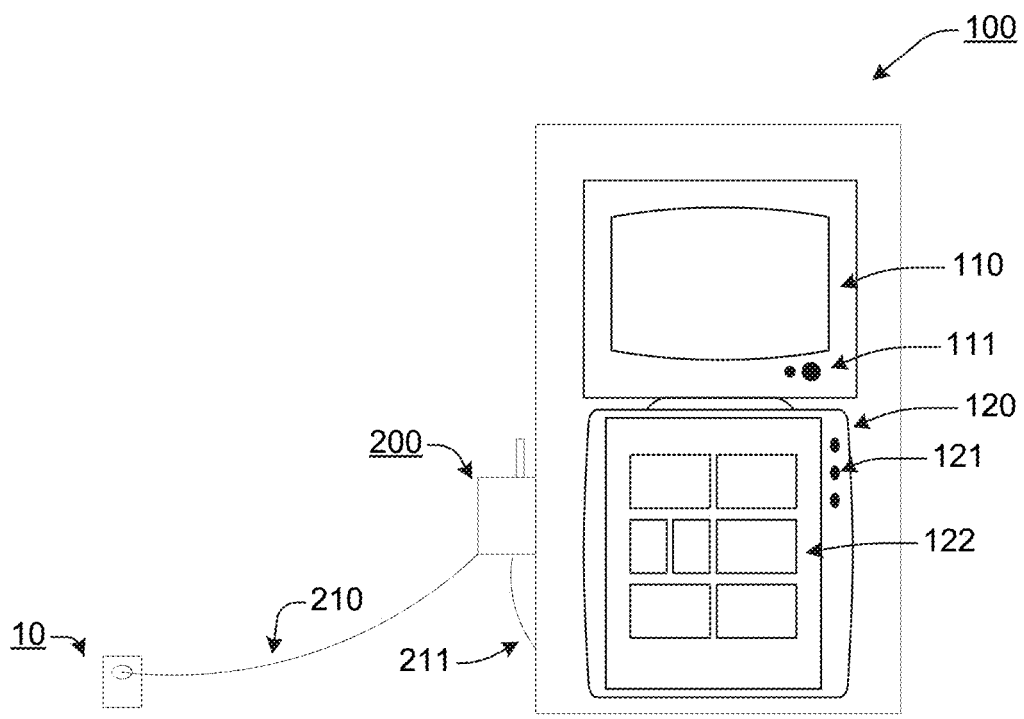
FIG. 1 is a top level system diagram of a monitoring device connected to an electronic display unit according to aspects of the invention.

Aspects of the present invention and their advantages may be understood by referring to the figures, wherein like reference numerals refer to like elements. The descriptions and features disclosed herein can be applied to various devices and machines located in various stores, businesses and other settings.

The present invention provides a monitoring system that includes a monitoring device that detects the electric current status of a nearby electric device or machine, and sends information related to the electric current status to a remote internet-accessible server via a wireless data communication network, whereupon the remote server analyzes the electric current status information related to the electric device in order to determine device usage and events associated with the electric device.

As seen in FIG. 1, an example is shown of monitoring device 200 that is connected to electronic display unit 100 according to an aspect of the invention. Electronic display unit 100 is an example of a typical electronic display device that is placed in a retail business location for providing information related to a company's products to consumers visiting that retail business location. In the example shown in FIG. 1, electronic display unit 100 includes a video display device 110 that plays recorded video content. For example, video display device 110 may be an LCD television with a memory for storing digital video content related to a brand product. In this regard, the memory may store more than one digital video program to be played on video display device 110. Electronic display unit 100 also includes a speaker 111 for playing audio content associated with a digital video program being played on video display device 110 or associated with separate digital audio content being played back by an audio playback unit provided in electronic display unit 100.

Electronic display unit 100 also includes control/feedback buttons 121 for controlling operation of video display device 110. For example, control/feedback buttons 121 can be operated by a user to select, start, stop and otherwise control the playback of one or more stored digital video programs on video display device 110. Control/feedback buttons 121 can also be operated by a user to select from menus shown on video display device 110 or to provide feedback in response to display prompts provided on the video display device 110 or in response to audio prompts provided by speaker 111. Electronic display unit 100 further includes display cabinet 120 that contains bins and/or shelves 122 for holding products and/or product literature and other items associated with the products. It should be appreciated that electronic display unit 100 does not necessarily have to include a video display device and may be any type of powered display unit that include, for example, lights, buttons, speaker, headphones, sensors, or any combination of these and/or other electric powered items.

Electronic display unit 100 obtains electricity from display electrical connection 211. In a typical use without monitoring device 200 of the present invention, display electrical connection 211 of electronic display unit 100 would be plugged directly into a power outlet to provide electricity to electronic display unit 100; however, in an aspect of the present invention shown in FIG. 1, display electrical connection 211 is instead plugged into monitoring device 200 which is in turn plugged into power outlet 10 (such as a local wall power outlet) via incoming electrical connection 210. In this manner, electronic display unit 100 receives electricity indirectly from power outlet 10 via monitoring unit 200, thereby allowing monitoring device 200 to monitor the electricity being consumed by electronic display unit 100 for determining the status and usage of various aspects of electronic display unit 100 such as, for example, the playback of a digital video program on video display device 110, the playback of audio content on speaker 111, or the operation of control/feedback buttons 121. In the alternative, electronic display unit 100 does not obtain electricity from a power outlet, and instead could include a battery to supply power to electronic display unit 100. In such a scenario, display electrical connection 211 is plugged into monitoring device 200 which is in turn plugged into the battery for a power supply. In this manner, electronic display unit 100 receives electricity indirectly from the battery via monitoring unit 200, thereby allowing monitoring device 200 to monitor the electricity being consumed by electronic display unit 100. In some aspects, a display unit that is powered by a battery may not include any powered features such as a video display, lights, buttons, speaker, sensors etc., and instead the power supplied by the battery is only used by monitoring device 200 to report on position/location tracking of the display unit.

As seen in FIG. 1, monitoring device 200 is provided on the outside of electronic display unit 100 to perform the monitoring activity referred to above. In this regard, monitoring device 200 may be detachably attached to electronic display unit 100 by known means such as adhesive strips or the like, or may be affixed to electronic display unit 100 by known means such as screws, or other connectors. In this manner, monitoring device 200 provides monitoring and communication capabilities to electronic display units that otherwise do not have such capabilities. Monitoring device 200 may be provided in several different forms, as is discussed further below.

Figure 2A:
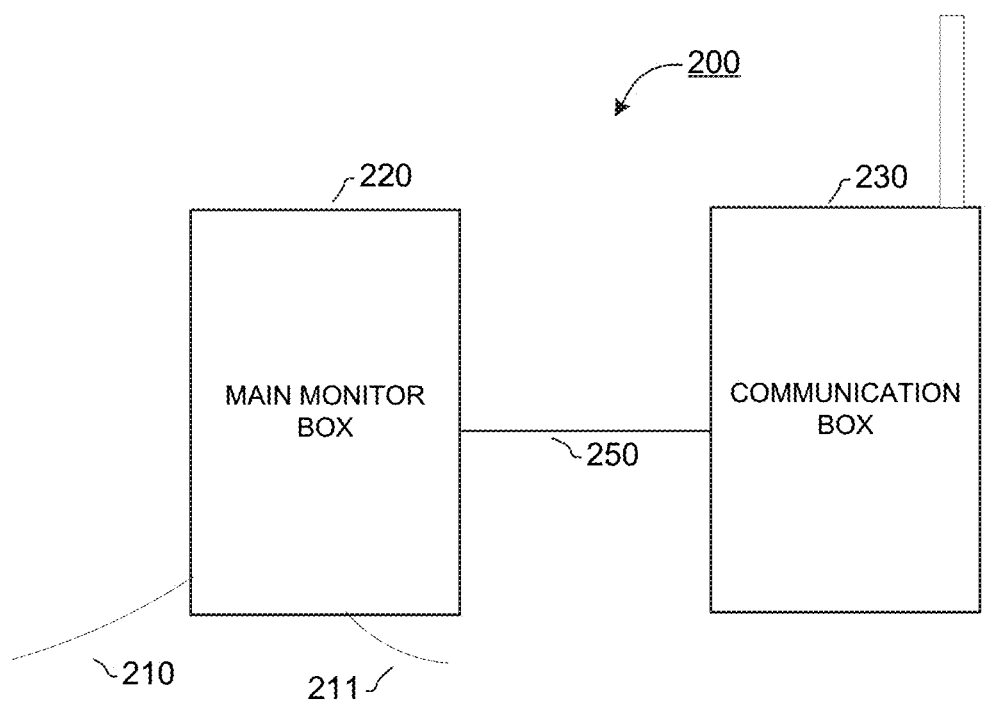
FIG. 2A is a block diagram illustrating a "two-box" version of a monitoring device according to aspects of the invention.

FIG. 2A depicts a "two-box" version of monitoring device 200 according to an aspect of the invention. In this "two-box" version, monitoring device 200 is comprised of two separate boxes comprising main monitor box 220 and communication box 230. In this configuration, main monitor box 220 is electrically interposed between power outlet 10 and electronic display unit 100 because display electrical connection 211 is plugged into main monitor box 220 and incoming electrical connection 210 is plugged into power outlet 10. In this manner, main monitor box 220 monitors the electricity being consumed by electronic display unit 100 for determining the status and usage of various aspects of electronic display unit 100. Also in this configuration, communication box 230 has the capability to communicate with a mobile cellular communication network in order to establish a connection with an internet-connected server. Communication box 230 also has Wi-Fi capability to detect and connect with local Wi-Fi access points, which access point information can be used to determine the location of monitoring device 200 (and therefore the location of electronic display unit 100 also). As seen in FIG. 2A, main monitor box 220 is connected to communication box 230 via inter-box communication connection 250 which can be a serial connection such as a UART (Universal Asynchronous Receiver-Transmitter) connection or a TTL Serial connection. Of course, other types of known communication protocols may be used for inter-box communication connection 250. Interbox communication connection 250 allows the transfer of data between main monitor box 220 and communication box 230, as is discussed more thoroughly below. In this two-box version, the two boxes do not necessarily need to be attached at the same location of electronic display unit 100. For example, main monitor box 220 may be attached to the lower portion of electronic display unit 100 where display electrical connection 211 is provided, and communication box 230 may be attached at an upper portion of electronic display unit 100 where its antenna would have the best reception and transmission quality. In such an aspect, inter-box communication connection 250 is long enough to provide the necessary connection between main monitor box 220 and communication box 230.

Figure 2B:
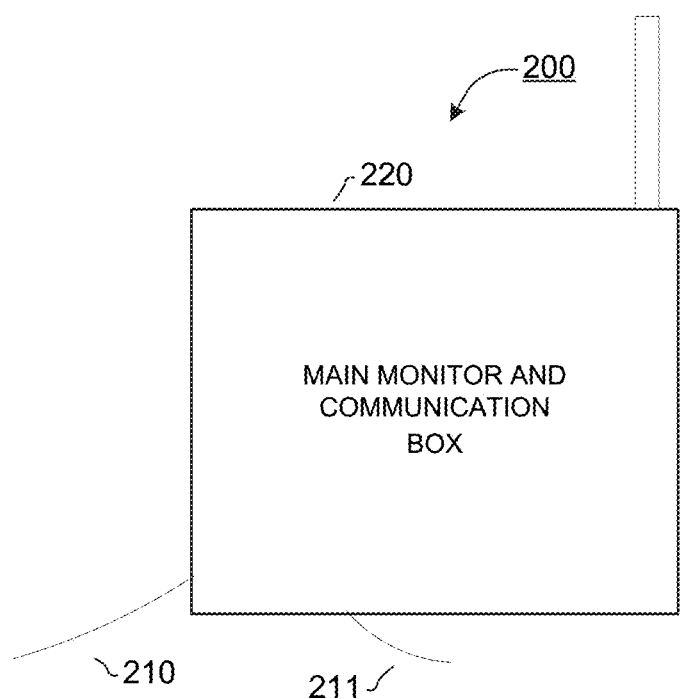
FIG. 2B is a block diagram illustrating a "one-box" version of a monitoring device according to aspects of the invention.

FIG. 2B depicts a "one-box" version of monitoring device 200 according to an aspect of the invention. In this "one-box" version, monitoring device 200 is comprised of a single main monitor and communication box 220. In this configuration, main monitor and communication box 220 is electrically interposed between power outlet 10 and electronic display unit 100 because display electrical connection 211 is plugged into main monitor and communication box 220 and incoming electrical connection 210 is plugged into power outlet 10. In this manner, main monitor and communication box 220 monitors the electricity being consumed by electronic display unit 100 for determining the status and usage of various aspects of electronic display unit 100. Also in this configuration, main monitor and communication box 220 has the capability to communicate with a mobile cellular communication network in order to establish a connection with an internet-connected server, and also has Wi-Fi capability to detect and connect with local Wi-Fi access points, which access point information can be used to determine the location of monitoring device 200 (and therefore the location of electronic display unit 100 also). Monitoring device 200 may also include a connection indication light to indicate the status of communication with a communication network, and also a power indication light to indicate the status of power at the monitoring device 200. In the case a multiple-box version of monitoring device 200, such as that discussed above with respect to FIG. 2A and below with respect to FIGS. 2C and 2D, the connection indication light and the power indication light may be located on one or more of the multiple boxes that comprise monitoring device 200, or may each be located on a separate one of the multiple boxes. For example, in the configuration shown in FIG. 2A, main monitor box 220 may contain a power indication light and communication box 230 may contain a connection indication light.

Figure 2C:
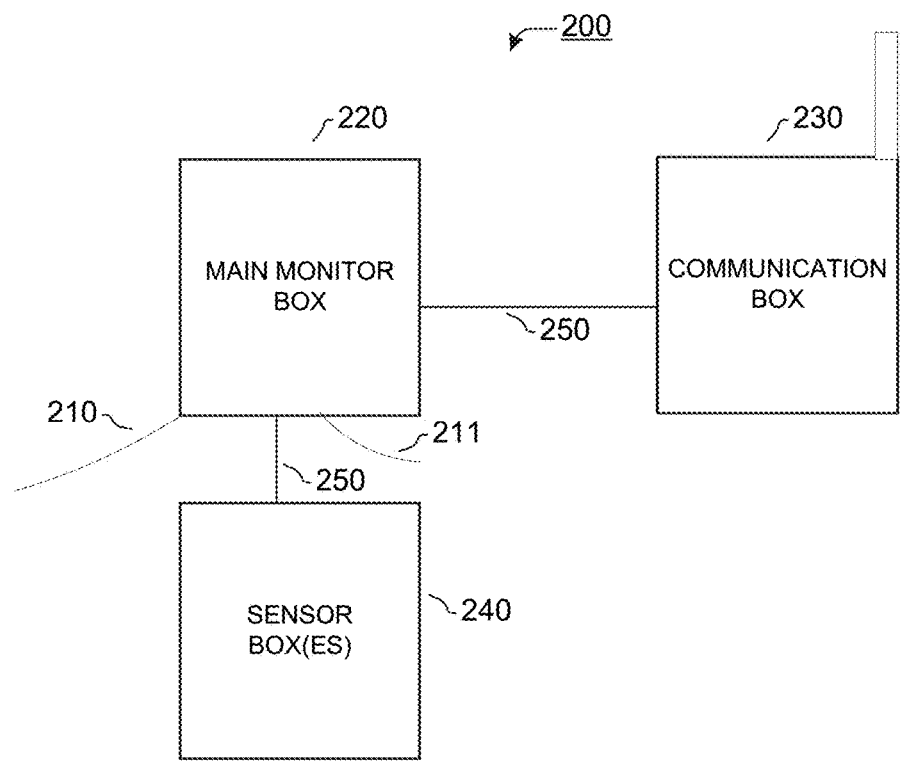
FIGS. 2C and 2D are block diagrams illustrating "three-box" versions of a monitoring device according to aspects of the invention.

FIG. 2C depicts a "three-box" version of monitoring device 200 according to an aspect of the invention. In this "three-box" version, monitoring device 200 is comprised of main monitor box 220, communication box 230 and sensor box 240. In this configuration, main monitor box 220 is electrically interposed between power outlet 10 and electronic display unit 100 because display electrical connection 211 is plugged into main monitor box 220 and incoming electrical connection 210 is plugged into power outlet 10. In this manner, main monitor box 220 monitors the electricity being consumed by electronic display unit 100 for determining the status and usage of various aspects of electronic display unit 100. Also in this configuration, communication box 230 has the capability to communicate with a mobile cellular communication network in order to establish a connection with an internet-connected server. Communication box 230 also has Wi-Fi capability to detect and connect with local Wi-Fi access points, which access point information can be used to determine the location of monitoring device 200 (and therefore the location of electronic display unit 100 also). As seen in FIG. 2C, main monitor box 220 is connected to communication box 230 via inter-box communication connection 250 which can be a serial connection such as a UART (Universal Asynchronous Receiver-Transmitter) connection or a TTL Serial connection. Of course, other types of known communication protocols may be used for inter-box communication connection 250. Inter-box communication connection 250 allows the transfer of data between main monitor box 220 and communication box 230, as is discussed more thoroughly below. This "three-box" version of monitoring device 200 also includes at least one sensor box 240 which includes one or more sensors for detecting various indications in the vicinity and environment in which monitoring device 200 is located. For example, one or more sensor boxes 240 can contain a proximity sensor to detect the proximity of a user in the vicinity of electronic display unit 100, a face detection sensor to detect whether a nearby user's eyes are viewing the screen of video display device 110, a light sensor to determine operating times of the store or business location in which electronic display unit 100 is located, or a weight sensor to determine when a product is present or removed from display cabinet 120. Of course, these are only examples of the types of sensors and their functionality, and other known sensors can be implemented in sensor box(es) 240. An inter-box communication connection 250 (such as described above) connects sensor box(es) 240 directly with main monitor box 220.

Figure 2D:
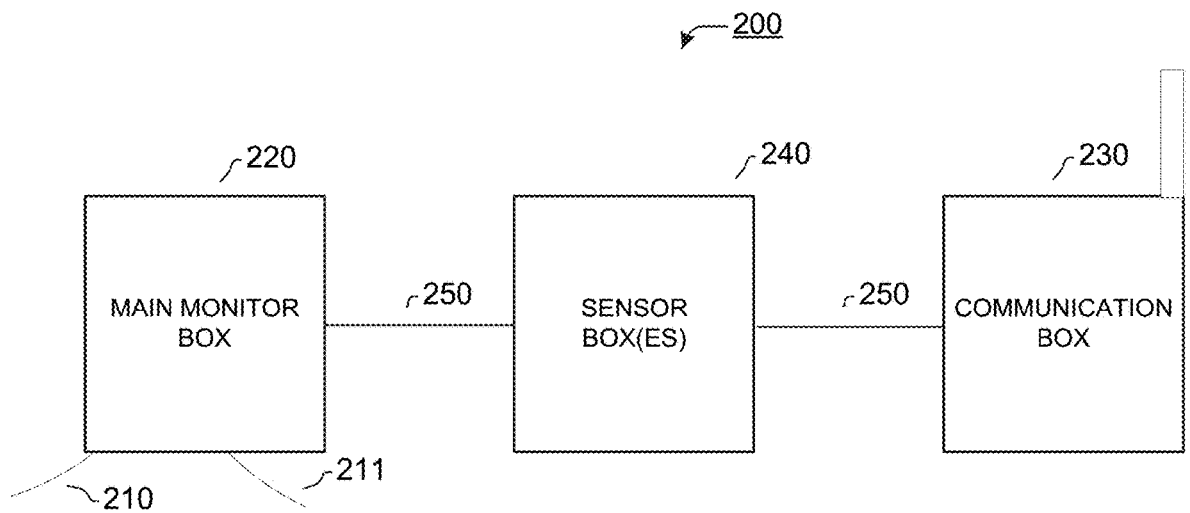

FIG. 2D depicts another "three-box" version of monitoring device 200 according to an aspect of the invention. Similar to FIG. 2C, monitoring device 200 in this "three-box" version is comprised of main monitor box 220, communication box 230 and sensor box 240. This configuration is the same as that described above with respect to FIG. 2C, except that sensor box(es) 240 share an inter-box communication connection 250 with both main monitor box 220 and communication box 230, instead of only having a direct connection with main monitor box 220 via a separate inter-box communication connection 250.

Figure 3:
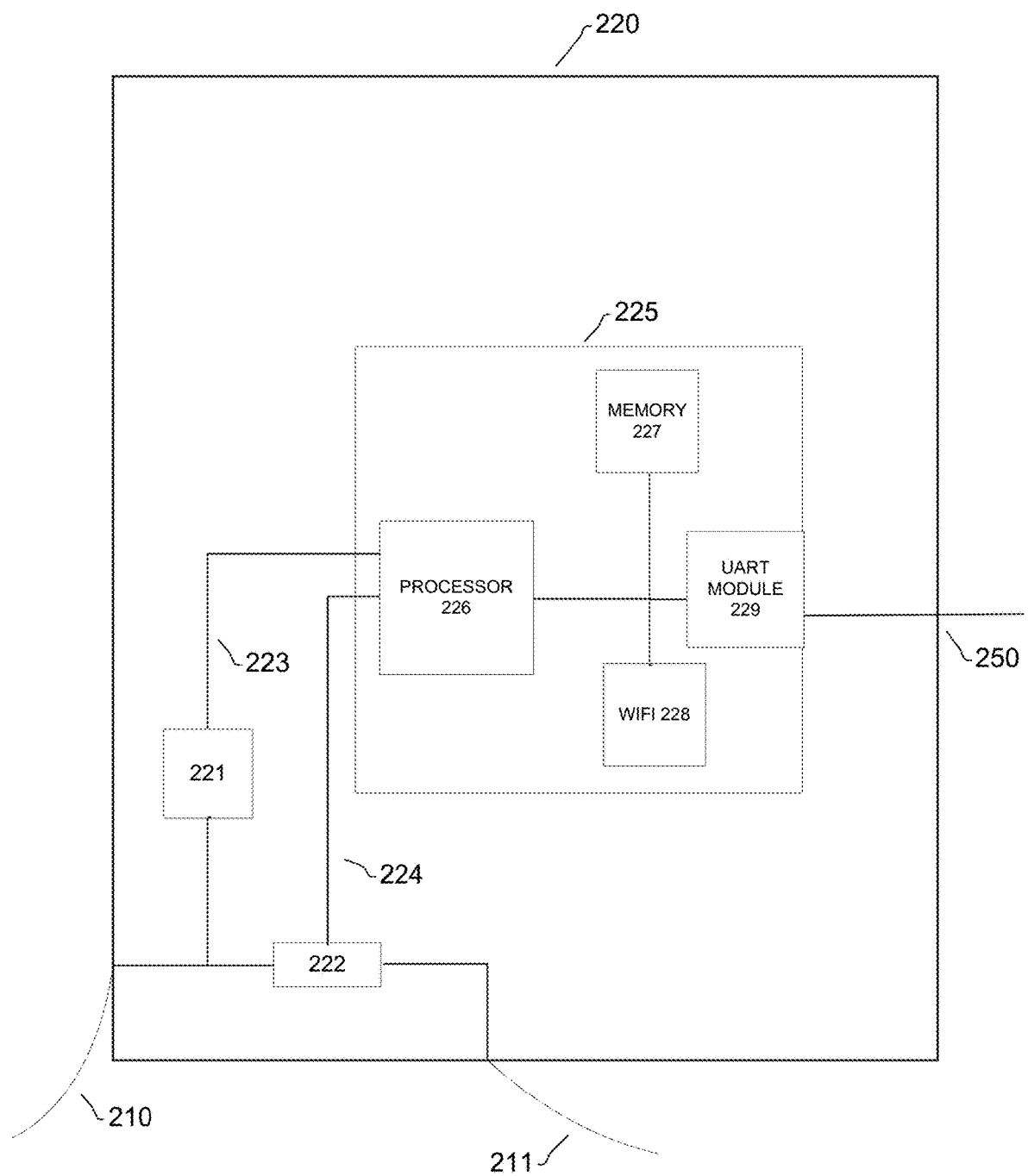
FIG. 3 is a detailed block diagram of a main monitor box according to aspects of the invention.

Turning to FIG. 3, a block diagram depicts the functional components of main monitor box 220 in a "two-box" or "three-box" version of monitoring device 200. As seen in FIG. 3, main monitor box 220 includes microcontroller 225 which is comprised of a microcontroller board on which is provided processor 226, Wi-Fi module 228, memory 227 and UART module 229. Of course, other types of known microcontrollers or custom boards with different component configurations can be used provided they have at least similar functionality as described herein. Memory 227 stores data and executable instructions, and processor 226 executes instructions from memory 227 to control and execute the functionality of monitor box 220 as described in more detail below. Wi-Fi module 228 has the capability to detect and connect with local Wi-Fi access points, which access point information can subsequently be used to determine the location of monitoring device 200 (and therefore the location of electronic display unit 100 also) as described in more detail below. UART module 229 provides capability to communicate with communication box 230 via inter-box communication connection 250. As discussed above, module 229 can instead be another type of serial protocol connection, or can instead support another type of known communication protocol for communication via inter-box communication connection 250. Microcontroller 225 shown in FIG. 3 includes at least one local communication bus through which processor 226, Wi-Fi module 228, memory 227 and UART module 229 communicate and exchange data with each other.

Main monitor box 220 shown in FIG. 3 is electrically interposed between power outlet 10 and electronic display unit 100 by having display electrical connection 211 plugged into main monitor box 220 and having incoming electrical connection 210 plugged into power outlet 10. In this manner, main monitor box 220 monitors the electricity being consumed by electronic display unit 100 for determining the status and usage of various aspects of electronic display unit 100. For this purpose, resistor 222 is provided between incoming electrical connection 210 and display electrical connection 211 to measure the electricity usage of electronic display unit 100 by outputting a current detection signal to processor 226 via current monitor line 224, the current detection signal being relationally based on the voltage across resistor 222. Resistor 222 may instead be another form or method of measuring current, such as a fiber optic current sensor, a Rogowski coil, or other known current sensors and current sensing techniques. Lastly, main monitor box 220 also includes power converter 221 which converts power obtained from incoming electrical connection 210 into the power level, such as voltage level, required to operate microcontroller 225. The output of power converter 221 is provided to microcontroller 225 via converted power line 223. In this manner, main monitor box 220 according to an aspect of the invention described above functions to monitor the electricity usage of electronic display unit 100 to which it is attached, and to send data related to this monitored electricity usage to communication box 230 via inter-box communication connection 250. It should be appreciated that main monitor box 220 may have another source or electricity, such as a local battery. In such a configuration, main monitor box 220 may utilize a sleep function in which processor 226 can initiate a wake-up function on a periodic basis in order to perform basic functions, such as to report on its current location which therefore would provide a stakeholder associated with the display unit, such as the brand product company identified with the display unit, with the current location of the display unit, such as where the display unit currently resides in the supply chain of the related retailer before deployment in a retailer store location.

Figure 4:
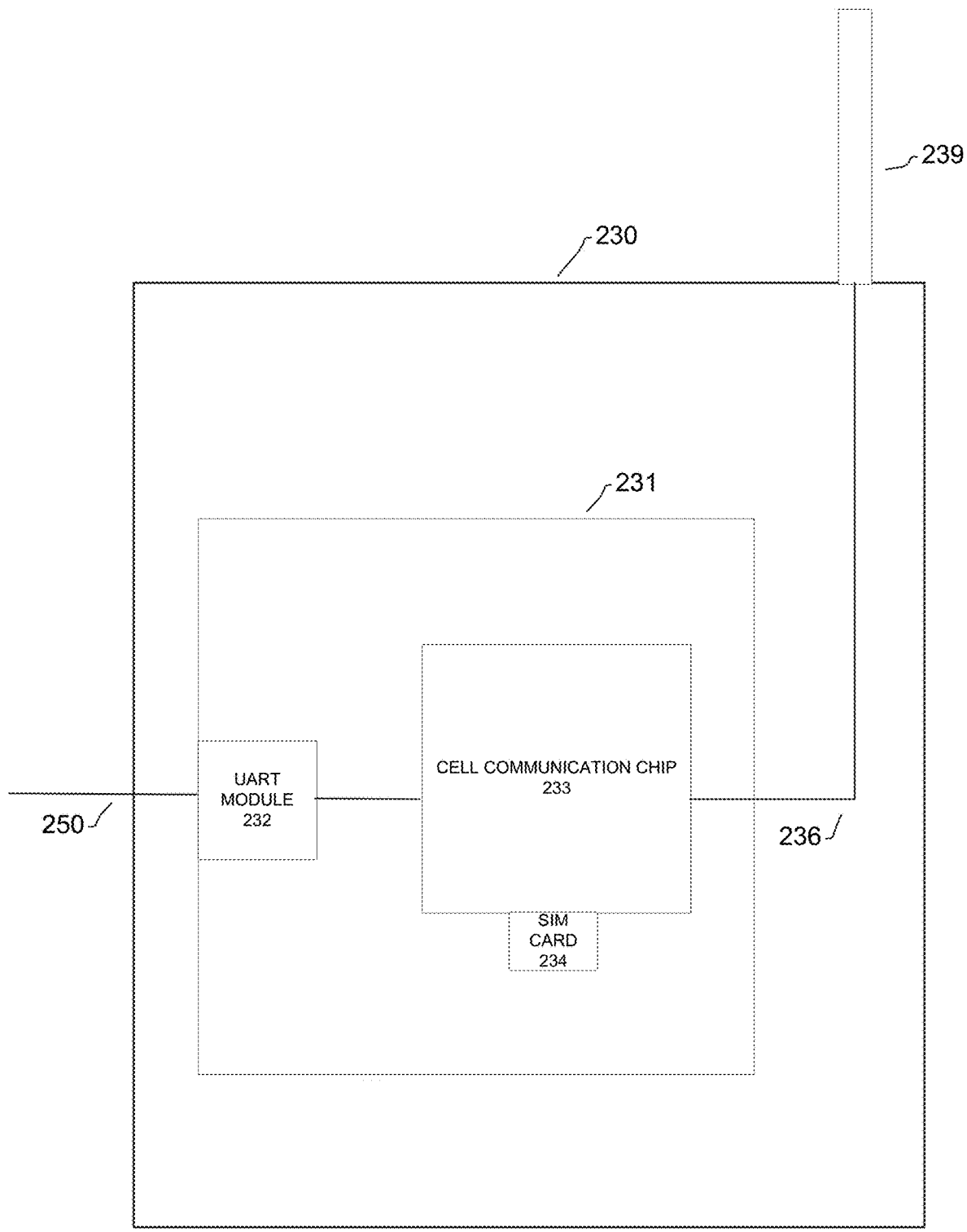
FIG. 4 is a detailed block diagram of a communication box according to aspects of the invention.

FIG. 4 is a block diagram depicting the functional components of communication box 230 in a "two-box" or "three-box" version of monitoring device 200. As seen in FIG. 3, communication box 230 includes powered circuit board 231 on which there is provided mobile cellular network communication chip 233 and UART module 232. Powered circuit board 231 is powered by electricity provided via inter-box communication connection 250. Similar to the discussion above with respect to UART module 229 of main monitor box 220, UART module 232 provides the capability to for communication between main monitor box 220 and communication box 230 via inter-box communication connection 250. As discussed above, UART module 232 can instead be another type of serial protocol connection, or can instead support another type of known communication protocol for communication via inter-box communication connection 250.

Mobile cellular network communication chip 233 may be a system-on-a-chip or other known combinations of processor, memory and interface components necessary to provide similar communication functionality for communicating via a mobile cellular network. Mobile cellular network communication chip 233 can be a chip that supports any type of mobile cellular network communication protocol, such as a 2G, 3G, 4G (such as LTE or WiMAX) or 5G protocol. Of course, other communication protocol technologies and standards can be used as well. Mobile cellular network communication chip 233 also has SIM card 234 connected to it for the purpose of configuration of mobile cellular network communication chip 233 and securely stores the international mobile subscriber identity (IMSI) number associated with monitoring device 220, and its related key for identification and authentication when communicating with the mobile cellular network. SIM card 234 can also store other data necessary for operation of mobile cellular network communication chip 233. Antenna 239 is used for transmitting and receiving signals necessary for communication with the mobile cellular network, and is connected to mobile cellular network communication chip 233 via antenna lead wire 236. In this manner, communication box 230 receives data related to the electricity usage of electronic display unit 100 from main monitor box 220 via inter-box communication connection 250, and then transmits the data to an internet-connected server via the mobile cellular network, as described in more detail below. In other aspects, monitoring unit 200 may also include a Bluetooth module. In the two-box version, the Bluetooth module may reside in either main monitor box 220 or communication box 230. Such a Bluetooth module may provide increased position accuracy of the location of monitoring unit 200 based on its relative location to another Bluetooth beacon within the retail location where the display unit (connected to the monitoring unit 200) is deployed. Also, in such aspects, the Bluetooth module may itself act as a beacon to be detected and/or connected with by passing consumers, such as a consumer with a smartphone that has a retailer application installed. Other known aspects of a Bluetooth beacon in such a scenario may also be implemented.

Figure 5:
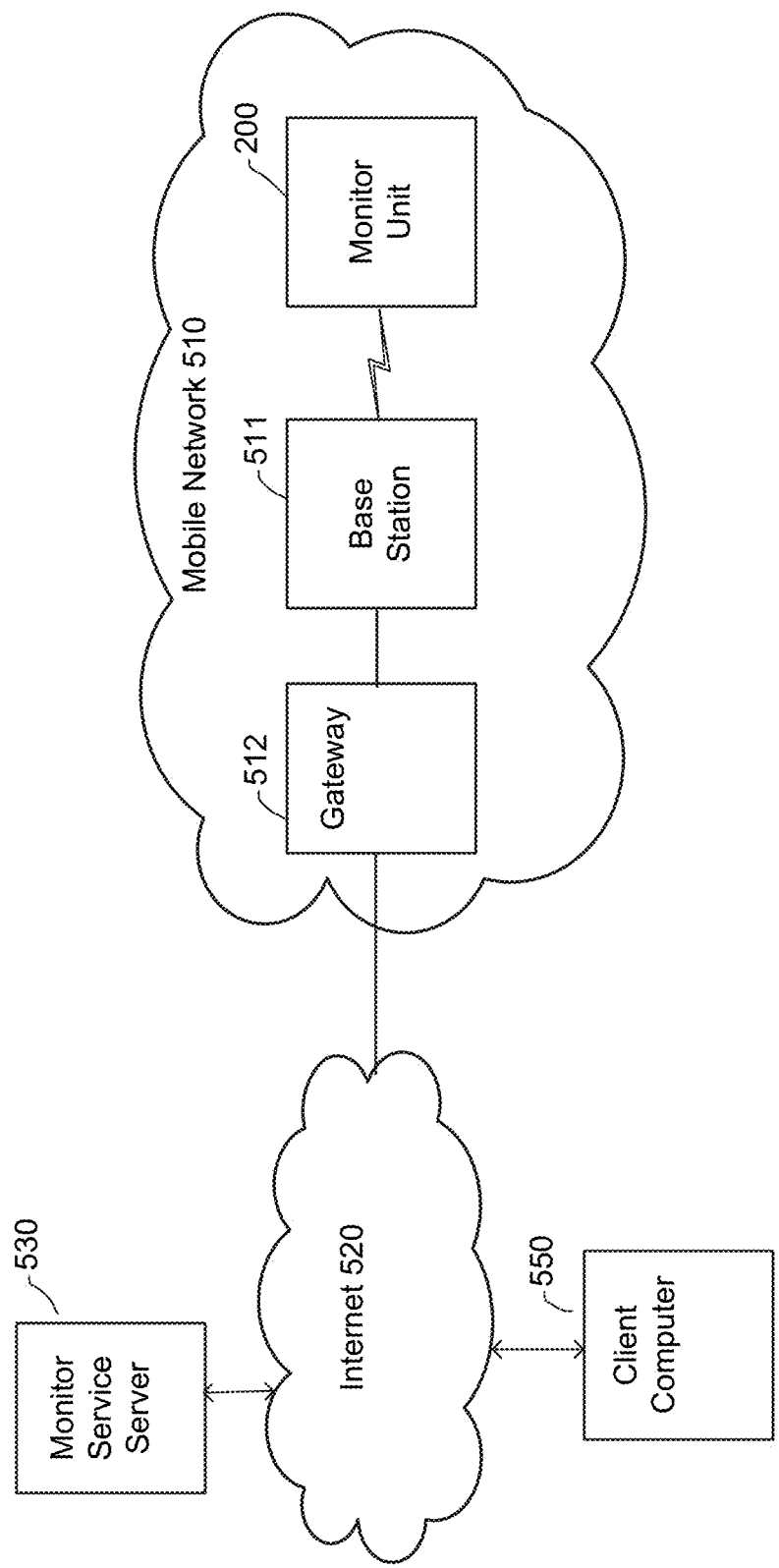
FIG. 5 is a top level communication network system through which the monitoring device communicates with a server according to aspects of the invention.

Turning to FIG. 5, a block diagram depicts a communication path between monitoring device 200 and remote, internet-connected monitor service server 530. In this regard, monitor service server 530 operates to receive data related to the electricity usage of electronic display unit 100 from monitoring unit 200 and to then analyze the data to determine usage status and usage events associated with electronic display unit 100. Monitor service server 530 can be utilized by the company which places monitoring devices 200 on electronic displays in various stores and businesses, or may be utilized by other entities such as product companies, marketing firms, business analyst agencies, and other interested stakeholders. Monitor service server 530 can be a physical or a virtual server, and may be located within the premises of the entity which utilized the server, or may be a cloud-based server operated and maintained by a third-party but utilized by one of the entities described above. In an aspect, monitor service server 530 is a known type of server, and includes at least one processor and one large memory unit, and also an internet connection module for connecting to the internet. Monitor service server 530 may also operate to send messages and data down to monitoring unit 200 such as, for example, initiation and or configuration messages and/or data to direct monitoring unit 200 to reboot, reconfigure or reassign itself for another installation or location. Similarly, monitor service server 530 may also operate to send software/firmware update messages and data down to monitoring unit 200 whereby the software and/or firmware of monitoring unit 200 can be updated. The functionality of monitor service server 530 according to aspects of the invention is described in more detail below.

As seen in FIG. 5, the monitoring unit 200 establishes a wireless connection and communicates with a nearby base station 511 in mobile cellular network 510. For example, known mobile cellular network companies operate cellular networks comprised of thousands of base stations for local, regional and national cellular coverage. Base station 511 is connected to gateway 512 within mobile cellular network 510, which connection may be wired or wireless. Gateway 512 also has a connection to internet 520, and in this manner, a cellular subscriber device, such as mobile cellular network communication chip 233 of monitoring unit 200 can wirelessly connect to internet 520 via mobile cellular network 510. Monitor service server 530 is shown to be connected to internet 530, and such connection can be a wired connection, such as by Ethernet, or can be a wireless connection such as a Wi-Fi or cellular network connection. Similarly, client computer 550 is shown to be connected to internet 530, and such connection can similarly be a wired connection, such as by Ethernet, or can be a wireless connection such as a Wi-Fi or cellular network connection. Client computer 550 is a computing device, such as a personal computer, a workstation, a tablet or a smartphone, operated by a client user who is a client of, or subscribes to, services offered by monitor service server 530. Client computer 550 can connect to monitor service server 530 via internet 520 to access and obtain data related to the usage status and usage events of one or more electronic display unit associated with a user of client computer 550, such as a product company or a marketing company. This functionality is described in more detail below.

Figure 6:
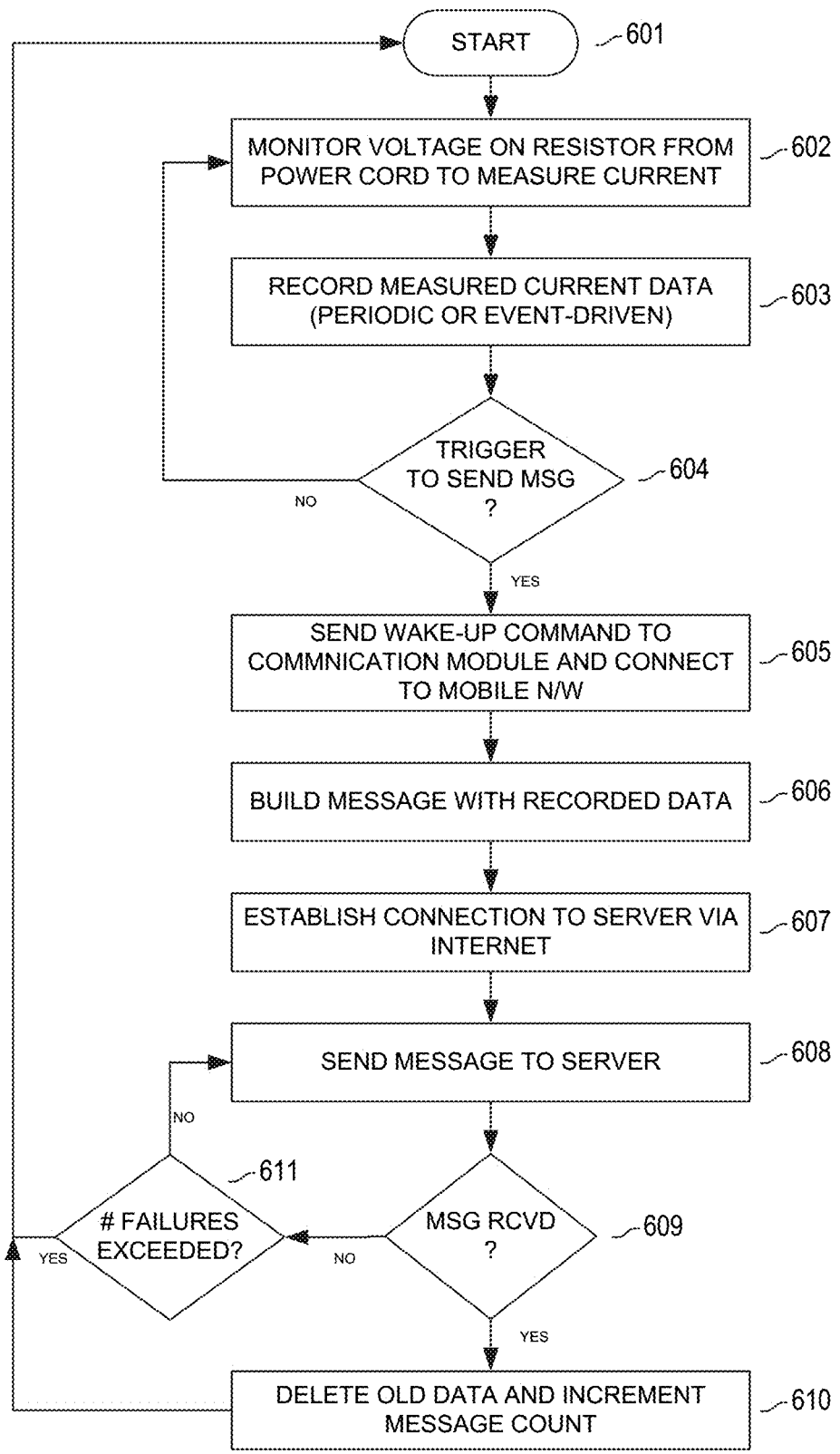
FIG. 6 is a flowchart that illustrates the process performed by a monitoring device to monitor the status of an electronic display unit according to aspects of the invention.

FIG. 6 is a flowchart that illustrates the functionality of monitoring unit 200 according to an aspect of the invention. The functionality described herein with respect to FIG. 6 applies generally to monitoring unit 200 regardless of the physical form of monitoring unit 200, such as the different physical versions of monitoring unit 200 as described above with respect to FIGS. 2A to 2D. The example process shown in FIG. 6 describing the functionality of monitoring unit 200, as executed by processor 226, starts at step 601. In step 602, the resistor 222 of monitoring unit 200 monitors the voltage between incoming electrical connection 210 and display electrical connection 211 and outputs a current detection signal on current monitor line 224 which is connected to processor 226. Next, in step 603, the value of the current detection signal on current monitor line 224 is measured and recorded in memory 227. The recording of the current detection signal value in step 603 can be performed on a periodic basis based on a predetermined time period value stored in memory 227, or can be performed based on an event trigger, such as the current detection signal value falling above or below one or more predetermined current threshold values stored in memory 227. Other trigger events can also be used to trigger the recording of the current detection signal value in step 603, such as an error condition of a previous recording step, or a request received at monitoring device 200 via mobile cellular communication network chip 233. Next, in step 604, it is determined whether a message trigger condition exists for sending a data message out to monitor service server 530 via mobile cellular network 510. A message trigger condition can be established by a lapse of time based on a long time period value, such as twelve hours for example, stored in memory 227. Also, a message trigger condition can be established by a determination that memory 227 reaches a capacity threshold value stored in memory 227. For example, if the capacity threshold value is ninety percent, then a message trigger condition is established when memory 227 is ninety percent full, which would occur as a result of the periodic recording of the current detection signal value in step 603.

If in step 604 it is determined that a message trigger condition is not established, the process returns to step 602 which is described above. Otherwise, if it is determined that a message trigger condition is established, the process proceeds to step 605 in which a wake-up command is sent to mobile cellular communication network chip 233 via inter-box communication connection to wake-up from a sleep/idle mode and to establish a connection with mobile cellular network 510. Next in step 606, a data message is built which includes necessary identification and/or protocol control data along with a message payload which contains the current detection signal values that were recorded since the last time a message was built. In an aspect, the message payload can also include access point identification information related to one or more local Wi-Fi access points that are detected by Wi-Fi module 228. This access point identification information can subsequently be used to determine the location of monitoring device 200 and electronic display unit 100 to which monitoring device 200 is attached.

The process then proceeds to step 607 in which monitoring unit 200 establishes a connection with remote, internet-connected monitor service server 530 through the wireless connection of mobile cellular communication network chip 233 with mobile cellular network 510. Next, in step 608, the data message that was built in step 606 is sent to monitor service server 530. In particular, processor 226 sends the data message to mobile cellular communication network chip 233 via inter-box communication connection 250, and also sends a "send" command to mobile cellular communication network chip 233 via inter-box communication connection 250, whereupon mobile cellular communication network chip 233 sends the data message to monitor service server 530 via mobile cellular network 510 and internet 520. In step 609, it is determined whether the data message was successfully received at monitor service server 530 by, for example, receiving an acknowledgement message back from monitor service server 530. In the case that the data message was successfully received at monitor service server 530, the process proceeds to step 610 in which the old stored data (the current detection signal values) that was placed into the data message is deleted from memory 227 and a message count is incremented, and then the process returns to step 601 to repeat the entire process again. If it is determined in step 609 that the data message was not successfully received at monitor service server 530, the process proceeds to step 611 in which it is determined whether a predetermined number of message failures has been exceeded. For example, a message failure count threshold value stored in memory 227 is compared to the number of times that a message was not successfully sent to monitor service server 530.

If, in step 611, it is determined that the message failure count threshold value has not been exceeded, the process returns to step 608 in which a new "send" command is issued to mobile cellular communication network chip 233 via inter-box communication connection 250 to re-send the data message. Otherwise, if in step 611 the message failure count threshold value has been exceeded, the process returns back to the start at step 601 to repeat the entire process, which therefore awaits a next message trigger condition is established to build a new data message to be sent to monitor service server 530. In this case, the old data is not deleted (because the prior data message was never successfully sent, and is therefore included in the new subsequent data message. The case in which the message failure count threshold value is exceeded in step 611 would correspond for example to a bad wireless connection with mobile cellular network 510, possibly due to temporary interference or excessive congestion in mobile cellular network 510 due to other cellular users in the vicinity.

Figure 7A:
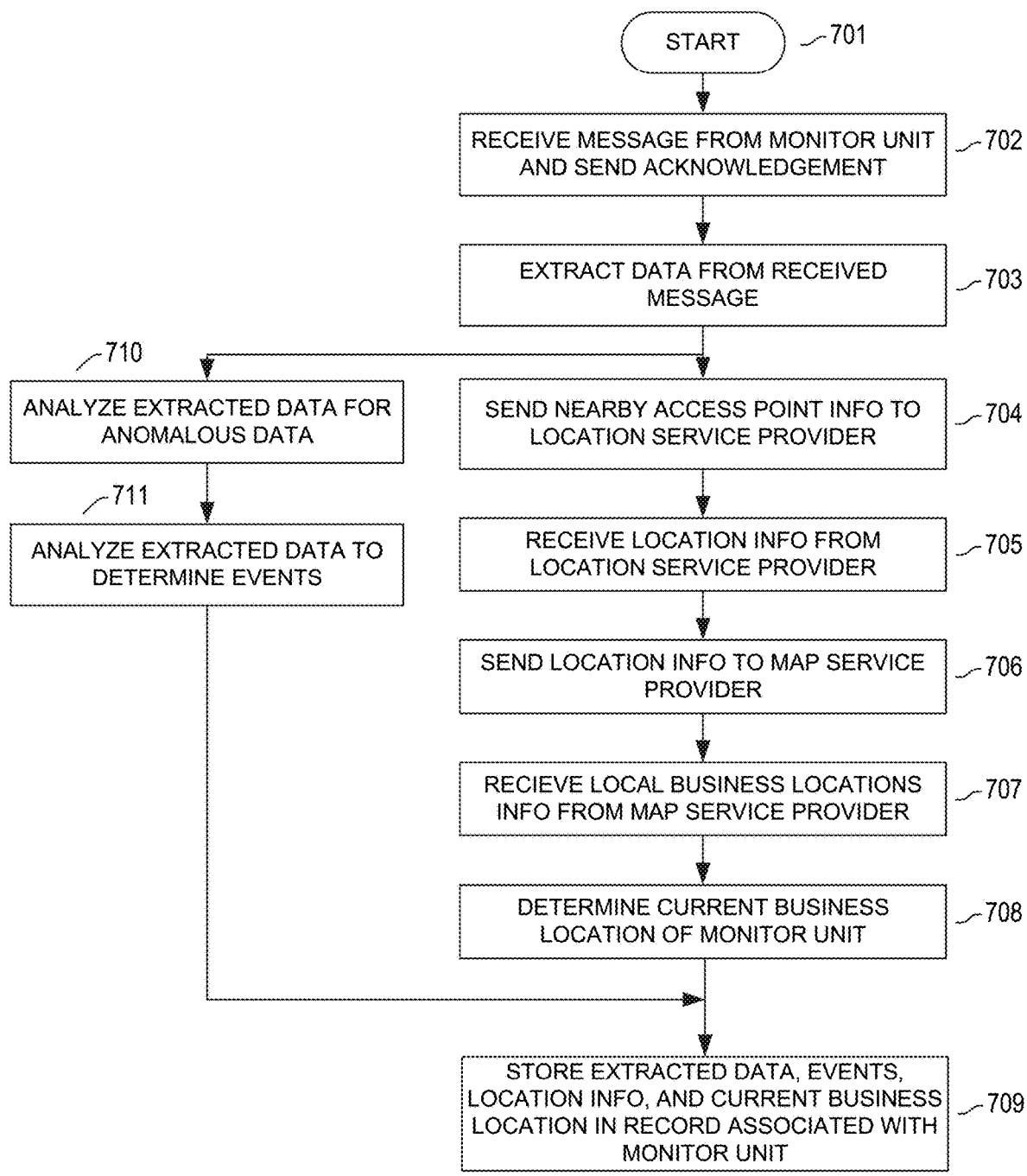
FIG. 7A is a flowchart that illustrates the process performed by a server to analyze data received from a remote a monitoring device according to aspects of the invention.

FIG. 7A is a flowchart that illustrates the functionality of monitor service server 530 according to an aspect of the invention. The functionality described herein with respect to FIG. 7 applies generally to monitoring unit 200 regardless of whether monitor service server 530 is a physical or virtual server, or where monitor service server 530 is located. The process starts in step 701, and proceeds to step 702 in which monitor service server 530 receives a data message from monitoring device 200. Specifically, monitor service server 530 receives, via its internet connection, the data message that was sent by monitoring device 200 through mobile cellular network 510 and then internet 520, as described above with respect to step 608 of FIG. 6. Next, in step 703, the current detection signal values and the access point identification information is extracted from the data payload of the received data message. The process next splits into parallel paths to both steps 704 and 710. In step 710, the extracted data is checked to see if it contains anomalous data. For example, each of the extracted current detection signal values is checked against preset range values to determine if they are outside a realist range of values, and if so, the current detection signal value is tagged as being anomalous and therefore can be excluded from subsequent processing. Next, in step 711, the extracted current detection signal values are analyzed to determine usage status and whether a usage event has occurred for the electronic display unit 100 associated with the monitoring unit 200 that sent the data message. In particular, the extracted current detection signal values are compared to current threshold values and timing patterns to determine whether a usage event, such as the playback of a video program has occurred at electronic display unit 100. The analysis in step 711 is described below in further detail with respect to FIG. 7B. The process then proceeds from step 711 to step 709.

The other parallel processing path proceeds at step 704 in which the extracted access point identification information is sent to a location service provider website via the internet.

In step 705 location information of the electronic display unit, such as latitude and longitude and an accuracy radius, are received from the location service provider website. The location information is then sent to a map service provider website via the internet in step 706, and the map service provider returns a list of local business identities that are in the vicinity of the location information, and the associated location information of the local business identities, in step 707. Next, in step 708, the location information of the electronic display unit is compared to the location information associated with the list of local business identities in order to determine the local business identity that is most likely at the location of the electronic display unit associated with the monitoring device that sent the data message. The process proceeds to step 709, in which the extracted the extracted current detection signal values and the extracted access point identification information, along with the location information, the determined local business identity, and the determined usage status and determined usage events are stored in a record associated with the monitoring device 200 within the memory of monitor service server 530. In this manner, the business is identified in which the electronic display device associated with the monitoring device is located, and a historic record of the usage status and usage events associated with the electronic display device is generated and saved in monitor service server 530 for subsequent access and analysis.

Figure 7B:
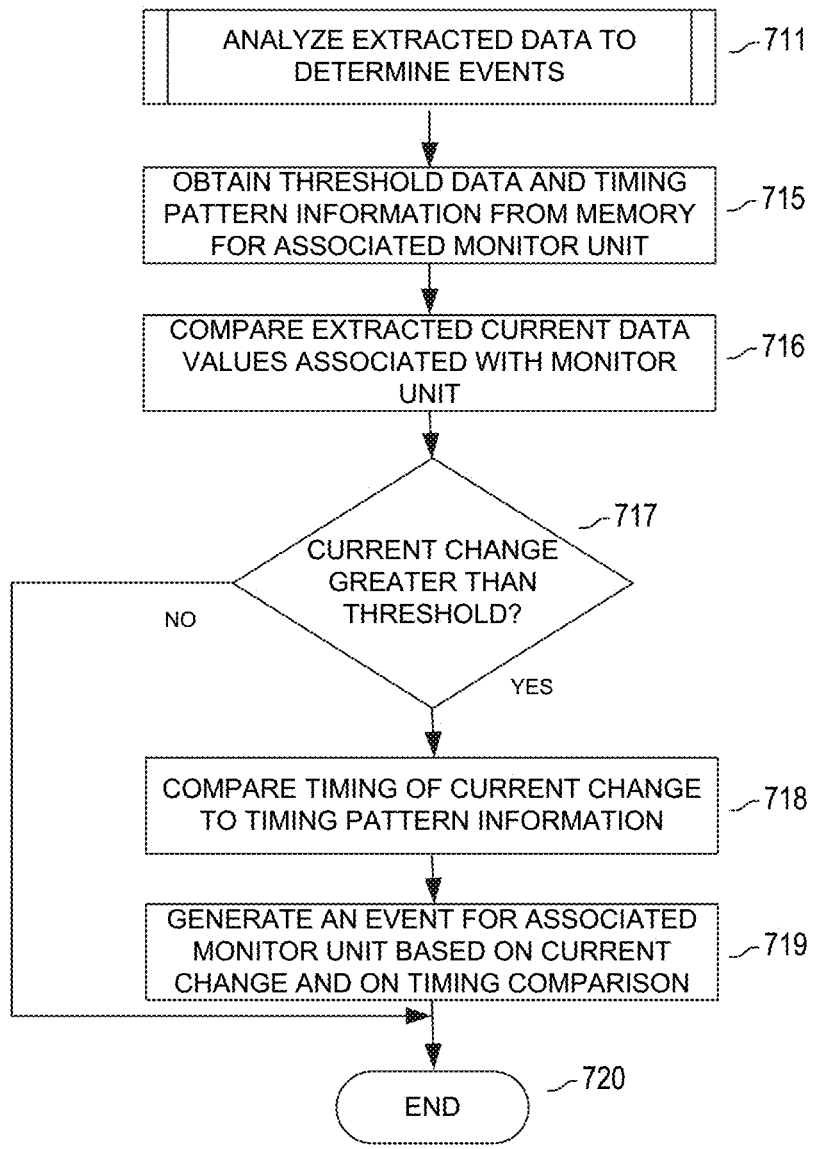
FIG. 7B is a flowchart that illustrates the process performed by a server to determine whether usage events have occurred at an electronic display unit according to aspects of the invention.

The analysis of extracted data in step 711 is now described in further detail with respect to FIG. 7B. In step 715 of FIG. 7B, current threshold values and timing patterns associated with the monitoring device that sent the data message are accessed from the memory of monitor service server 530. In this regard, the memory of monitor service server 530 can contain numerous different sets of current threshold values and timing patterns, each set being associated with a different type of electronic display unit to which a monitoring device is attached. Accordingly, a set of current threshold values and timing patterns is tailored to a particular type of electronic display unit. For example, electronic display unit 100 shown in FIG. 1 has a video display device 110 that will have a particular set of current threshold values and timing patterns that are used to determine by comparison against recorded current values associated with electronic display unit 100 whether and when the video display has been engaged in playback of a video program, and even to determine which video program was played based on time duration of playback. Similarly, the particular set of current threshold values and timing patterns can be used to determine when speaker 111 was operational and for how long, when certain ones of control/feedback buttons 121 have been operated, and when any sensors of sensor box(es) 240 have been triggered.

Next, in step 716, the individual current detection signal values are compared to the accessed current threshold values for the electronic display device associated with the monitoring device that sent the data message. In step 717, it is determined whether a current change has occurred based on the comparisons in step 716 that is greater than one or more of the accessed current threshold values. If the answer in step 717 is yes, the process proceeds to step 718 in which the timing of the one or more identified current changes is compared to one or more of the accessed timing patterns. Based on the comparison against the timing pattern(s) in step 718, at least one usage event associated with the electronic display device to which the monitoring device is attached is generated. For example, based on the current change exceeding a specific current threshold value it can be determined that video display device 110 of electronic display unit 100 was in operation over a given time period, and then based on the comparison to a timing pattern in step 718 it can be determined that video display device 110 played a specific one of several digital video programs stored available at electronic display unit 100. As mentioned above, a similar process is employed to determine whether other usage events associated with the different functions of electronic display unit 100 have occurred, such as operation of speaker 111, operation of control/feedback buttons 121, and the trigger and feedback output of sensor box(es) 240.

Figure 7C:
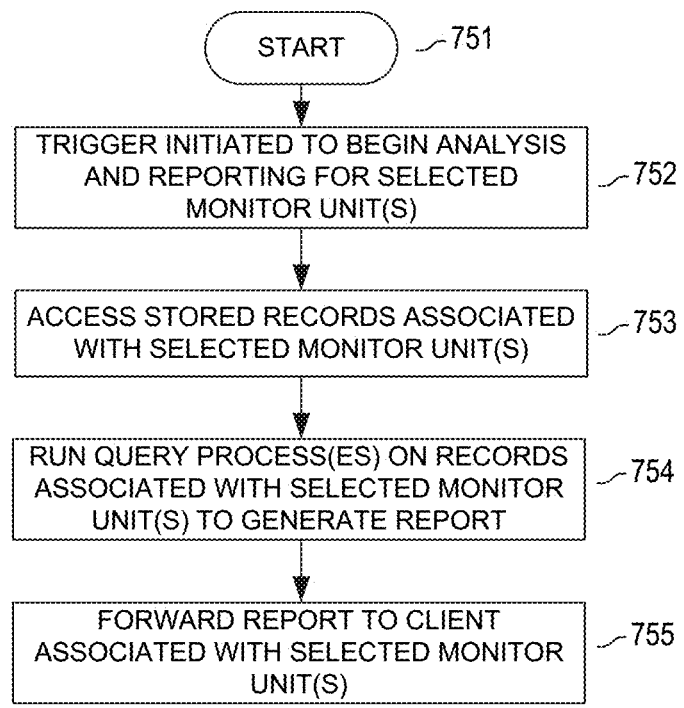
FIG. 7C is a flowchart that illustrates the process performed by a server to analyze stored data associated with one or more electronic display units and generate reports according to aspects of the invention.

FIG. 7C is a flowchart that describes the process for monitor service server 530 to run queries in which the stored data associated with one or more electronic display units is analyzed and one or more reports are generated based on the analyzed data. In particular, client computer 550 can access monitor service server 530 and request a query to analyze usage data associated with a group of electronic display units that the user of client computer 550 is interested in. For example, the user of client computer 550 may represent a company that has several hundred electronic display units of the same type for displaying a specific product made by that company distributed in stores and business at different locations nationwide, or even globally. Such a user can therefore initiate a query to analyze the stored data associated with all of those several hundred electronic display units to determine which ones are being operated most often, which videos are being displayed most often and what types of feedback is obtained.

In step 752 of FIG. 7C, a trigger is initiated to begin the analysis and report generation for data received from monitoring devices associated with a selected group of electronic display devices. As mentioned above, the trigger can be initiated from a user of client computer 550, or can be initiated based on the lapse of time since the last trigger for analysis of the same group of electronic display devices, or can be initiated based on the memory of monitor service server 530 storing a certain number of records associated with one or more electronic display devices. In step 753, the records associated with the selected group of electronic display devices are accessed from the memory of monitor service server 530. Next, in step 754, a query process associated with the trigger is run on the usage data in the records associated with the selected group of electronic display devices in which statistical operations are run on the usage data to generate reports. For example, the reports can include statistical activity summaries and graphic plots and representations of the statistical activity summaries, such as electronic display unit activity summaries based on total numbers, types of business location, geography, types of functions utilized, operational errors, etc. Lastly, in step 755, the generated reports are forwarded to the client associated with the selected group of electronic display devices. For example, if the requesting user is the user of client computer 550, the generated reports are forwarded to the client computer 550 via internet 520.

Figure 8A:
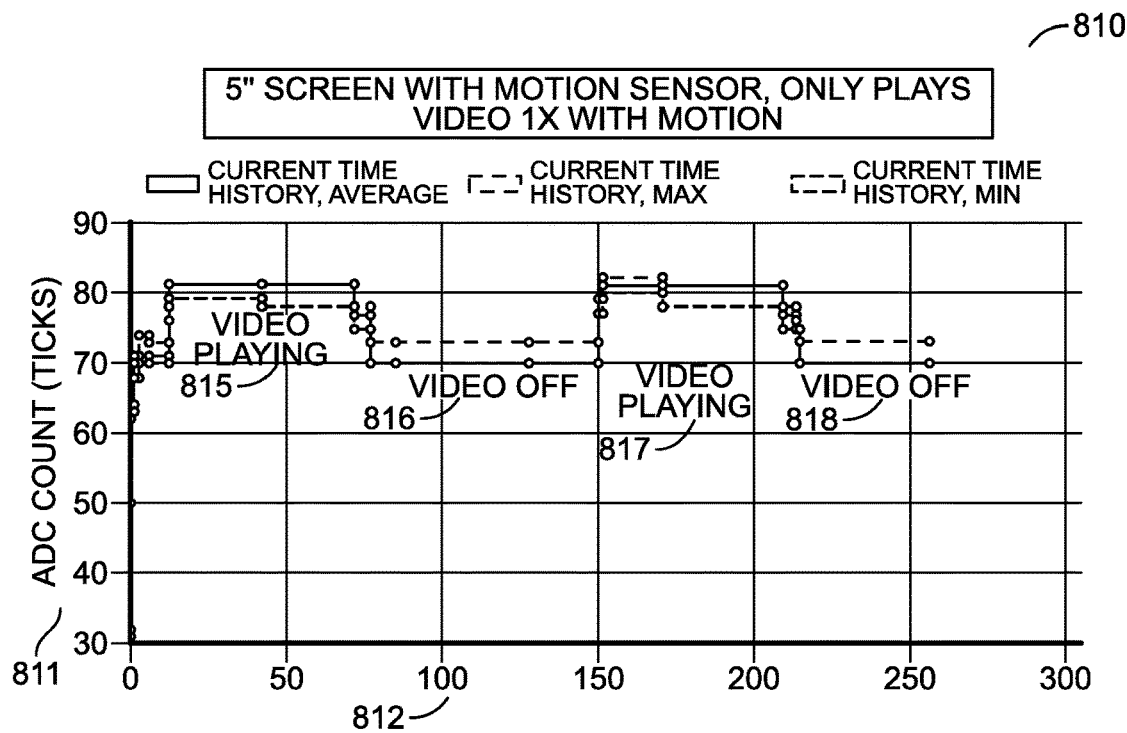
FIGS. 8A to 8E are plots that illustrate determining usage events based on electric current data associated with an electronic display unit according to aspects of the invention.
Figure 8B:
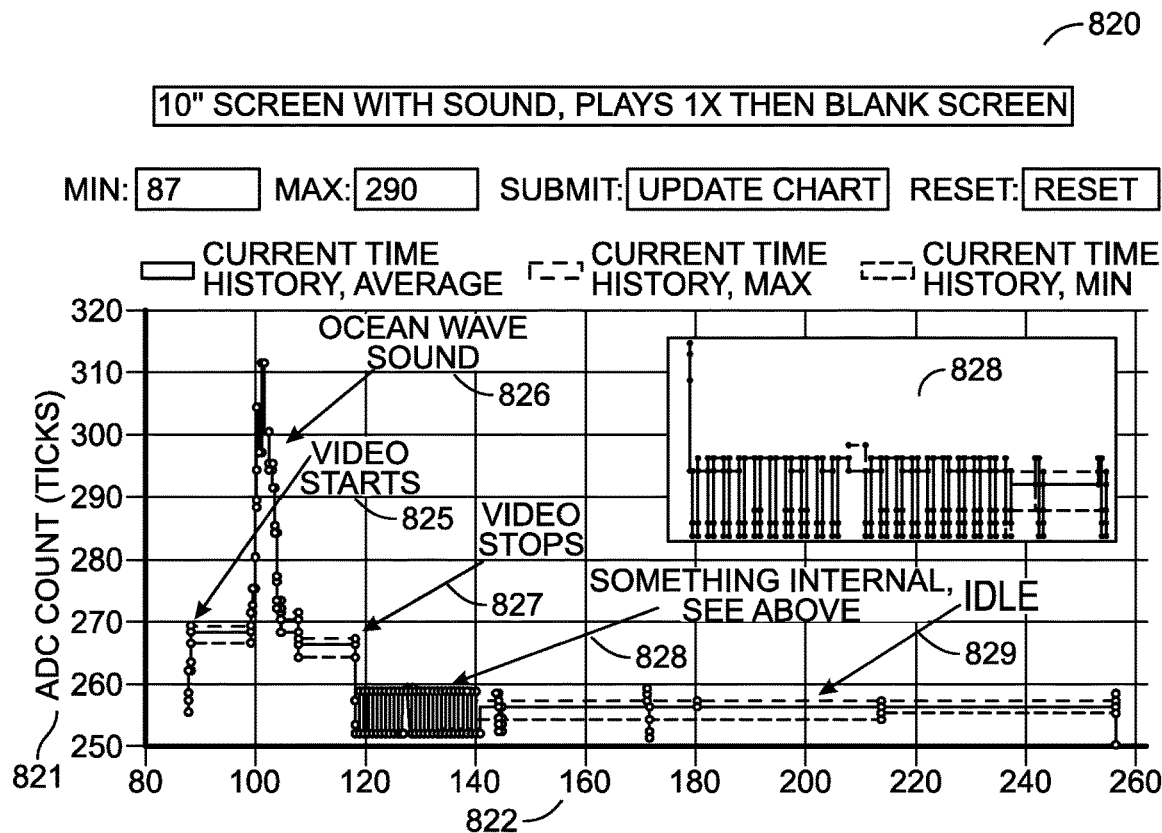

FIGS. 8A to 8E are plots of current data (on the vertical axis) against time (on the horizontal axis) according to aspects of the invention. These plots illustrate different types of usage events based on current data received from a monitoring device associated with an electronic display unit. In FIG. 8A, plot 810 is shown which shows current data 811 received from a monitoring device associated with an electronic display unit that has a video display device, as recorded against time 812 (seconds). As seen in plot 810, the two relatively high current steps 815 and 817 indicate the playing of a video program on the video display device of the electronic display unit. The low current steps 816 and 818 outside of the video playing segments indicate that the video is off (not playing). In FIG. 8B, plot 820 is shown which shows current data 821 received from a monitoring device associated with an electronic display unit that has a video display device and a speaker, as recorded against time 822 (seconds). As seen in plot 820, the relatively raised square current step between the video start 825 and the video stop 827 indicates the playing of a video program on the video display device of the electronic display unit, and the current spike 826 indicates the playing of specific audio content (for example, an ocean wave sound) on the speaker of the electronic display unit. The high frequency current section 828 (shown in more detail in the inset diagram) indicates certain internal electric activity occurring in the electronic display unit, and the extended, flat current section 829 indicates an idle time of the video display device of the electronic display unit during which no video program is being played.

Figure 8C:
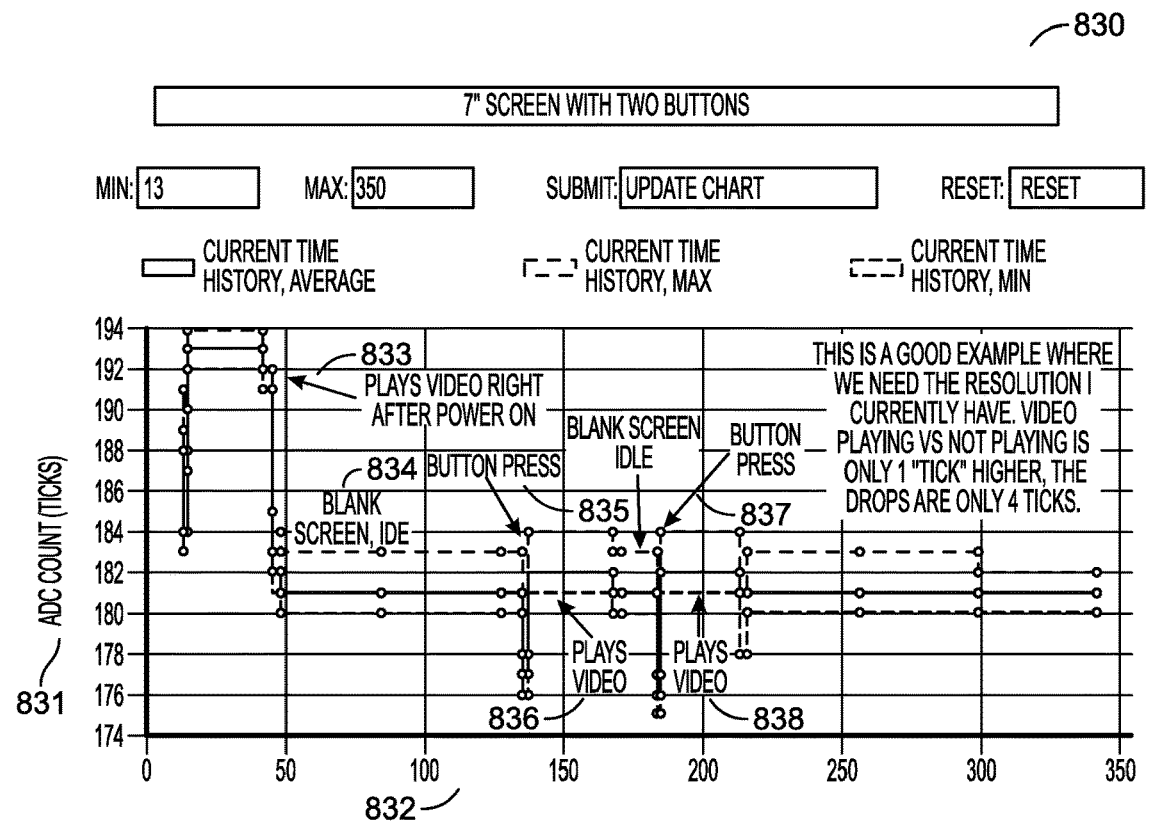

In FIG. 8C, plot 830 is shown which shows current data 831 received from a monitoring device associated with an electronic display unit that has a video display device and two control/feedback buttons, as recorded against time 832 (seconds). As seen in plot 830, the relatively raised square current steps 833, 836 and 838 indicate the playing of a video program on the video display device of the electronic display unit after a power on event (as in the case of video play segment 833) or after a button press 835, 837 (as in the case of video play segment 836 and 838), and the lower current sections 834 indicate the an idle time of the video display device of the electronic display unit during which no video program is being played.

Figure 8D:
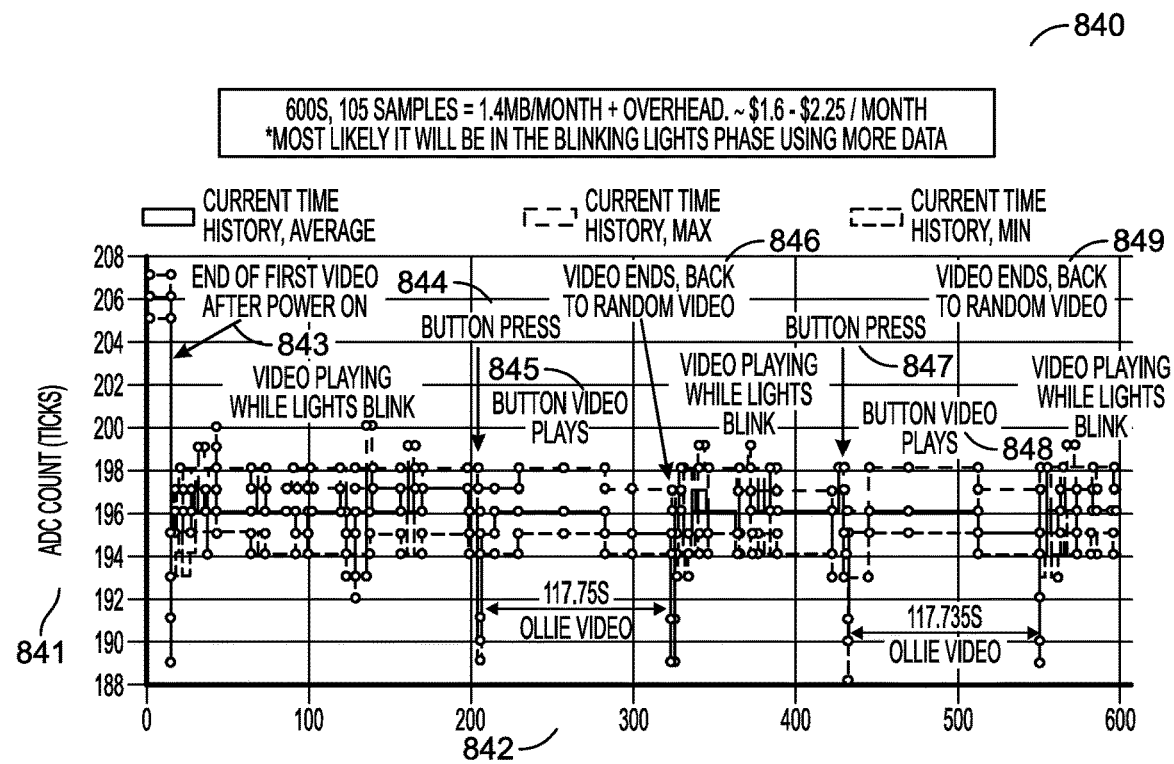

FIG. 8D shows plot 840 which shows current data 841 received from a monitoring device associated with an electronic display unit that has a video display device, control/feedback buttons and blinking lights, as recorded against time 842 (seconds). As seen in plot 840, the current drop 843 indicates the end of a first video playback after a power on event. The most active variable current sections in plot 840 indicate that a background video is playing while the blinking lights are active. Instances of a button press 844, 847 are indicated by a current change, after which an associated relatively raised current step 845, 848 indicates the playing of a video program that is associated with the button that was pressed. When the current indicates that the button-associated video ends 846, 849, the video display device resumes playing a background video and the blinking lights are active.

Figure 8E:
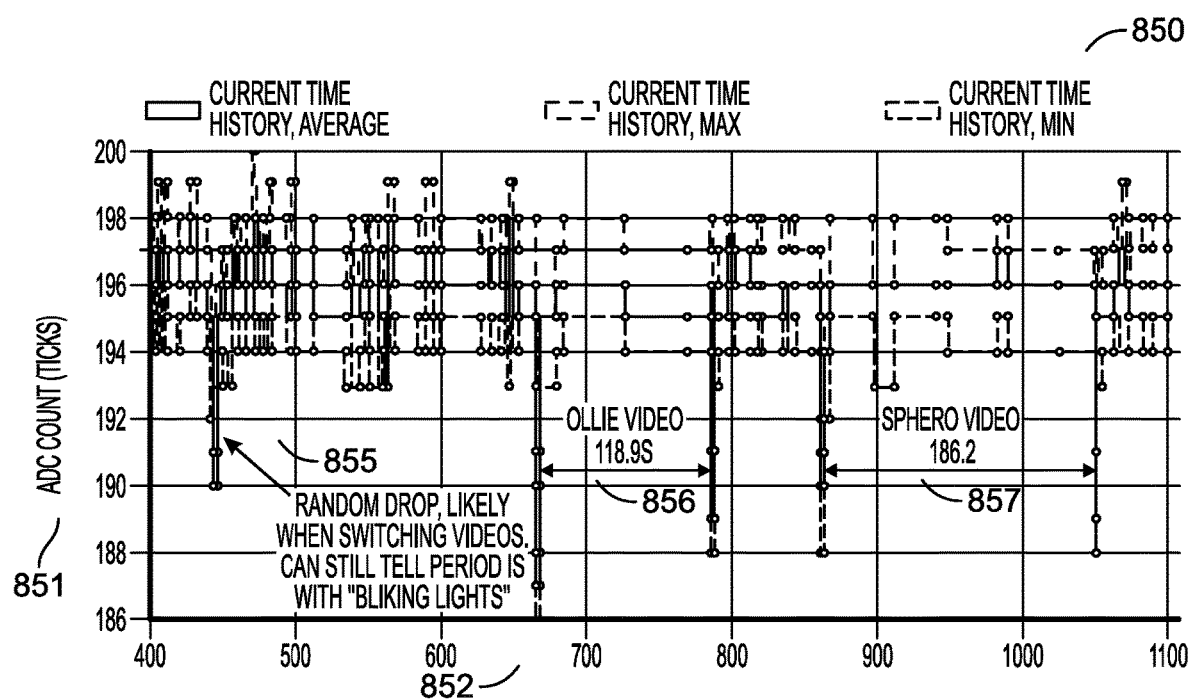

FIG. 8E shows plot 850 which shows current data 851 received from a monitoring device associated with an electronic display unit that has a video display device and control/feedback buttons, and blinking lights, as recorded against time 852 (seconds). As seen in plot 850, the random current drop 855 indicates the switching of video programs being played on the video display device of the electronic display unit while blinking lights are operating. Relatively raised current step 856 indicates the playing of a first video program on the video display device of the electronic display unit that has a specific first time duration, and the relatively raised current step 857 indicates the playing of a second video program on the video display device of the electronic display unit that has a specific second time duration. The remaining current sections in plot 850 indicate the playing of a random background video program on the video display device of the electronic display unit.

According to the above descriptions and accompanying figures, the monitoring device and system described herein provides remote monitoring capability for electronic display units located in remote locations for determining usage status and events associated with the operation of different functions of the electronic display units. It can also be appreciated by those skilled in the art that the monitoring device and system can also be used to remotely monitor the operational functionality of many other types of electric devices and machines, such as vending machines, health care machines and devices, and information kiosks.

Those of skill will appreciate that the various illustrative logical blocks, modules, units, and algorithm steps described in connection with the aspects disclosed herein can often be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular constraints imposed on the overall system. Skilled persons can implement the described functionality in varying ways for each particular system, but such implementation decisions should not be interpreted as causing a departure from the scope of the invention. In addition, the grouping of functions within a unit, module, block, or step is for ease of description. Specific functions or steps can be moved from one unit, module, or block without departing from the invention.

The various illustrative logical blocks, units, steps and modules described in connection with the aspects disclosed herein, and those provided in the accompanying documents, can be implemented or performed with a processor, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein, and those provided in the accompanying documents. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm and the processes of a block or module described in connection with the aspects disclosed herein, and those provided in the accompanying documents, can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC. Additionally, device, blocks, or modules that are described as coupled may be coupled via intermediary device, blocks, or modules. Similarly, a first device may be described a transmitting data to (or receiving from) a second device when there are intermediary devices that couple the first and second device and also when the first device is unaware of the ultimate destination of the data.

The above description of the disclosed aspects, and that provided in the accompanying documents, is provided to enable any person skilled in the art to make or use the invention. Various modifications to these aspects will be readily apparent to those skilled in the art, and the generic principles described herein, and in the accompanying documents, can be applied to other aspects without departing from the spirit or scope of the invention. Thus, it is to be understood that the description and drawings presented herein, and presented in the accompanying documents, represent particular aspects of the invention and are therefore representative examples of the subject matter that is broadly contemplated by the present invention. It is further understood that the scope of the present invention fully encompasses other aspects that are, or may become, obvious to those skilled in the art and that the scope of the present invention is accordingly not limited by the descriptions presented herein, or by the descriptions presented in the accompanying documents.

What we claim is:

1. A remote monitoring device for monitoring an electronic product display device to which the remote monitoring device is detachably connected, the remote monitoring device comprising:
   a current detector detachably connected to an input power cord that provides power to said electronic product display device, the current detector outputting a current signal based on a current of the input power cord, wherein the current of the input power cord varies based on interaction of a user with the electronic product display device;
   a cellular communication chip that communicates via a cellular communication network to an internet-connected server;
   a Wi-Fi communication module that communicates with one or more local Wi-Fi access points and obtains access point identification information related to the one or more local Wi-Fi access points;
   a memory that stores data and processor-executable instructions; and
   a processor in communication with the current detector, the cellular communication chip, the Wi-Fi communication module and the memory, the processor configured to execute the processor-executable instructions to (1) periodically record an electric current value associated with the current signal, each recorded electric current value having an associated recorded time value, (2) generate a message containing each recorded electric current value and its associated recorded time value, and also containing the access point identification information, (3) provide the message to the cellular communication chip, and (4) instruct the cellular communication chip to send the message via the cellular communication network to the internet-connected server for processing by the internet-connected server to determine whether a usage event has occurred from the user interaction with the electronic product display device.

2. The remote monitoring device of claim 1 further comprising:
   a main monitor box that contains the current detector, the memory and the processor; and
   a communication box connected to the main monitor box via an inter-box communication connection, wherein the communication box contains the cellular communication chip and the Wi-Fi communication module.

3. The remote monitoring device of claim 2 wherein the main monitor box further contains a first serial connection and the communication box further contains a second serial connection, and wherein the inter-box communication connection is established between the first serial connection and the second serial connection.

4. The remote monitoring device of claim 1, wherein the remote monitoring device further comprises a sensor box that contains at least one sensor, the at least one sensor being one of a proximity sensor, a motion sensor, a face detection sensor, a light sensor and a weight sensor.

5. A method for monitoring an electronic product display device, the method comprising the steps of:
   monitoring a current of an input power cord that provides power to the electronic product display device and outputting a current signal based on the current of the input power cord, wherein the current of the input power cord varies based on interaction of a user with the electronic product display device;
   obtaining access point identification information related to one or more local Wi-Fi access points detected by a Wi-Fi communication module;
   recording, on a frequent basis, an electric current value associated with the current signal, and recording a time value associated with each recorded electric current value;
   generating a message containing each recorded electric current value and its associated recorded time value, and also containing the access point identification information;
   providing the message to a cellular communication chip; and
   instructing the cellular communication chip to send the message via a cellular communication network to an internet-connected server for processing by the internet-connected server to determine whether a usage event has occurred from the user interaction with the electronic product display device.

6. The method of claim 5, wherein the input power cord is monitored by measuring a voltage on a resistor that is in electrical connection with the input power cord and with the electronic product display device, and wherein the current signal indicates a current level based on the measured voltage.

7. The method of claim 5, wherein the input power cord is monitored by a current sensing device that is in electrical connection with the input power cord and with the electronic product display device, and wherein the current signal indicates a current level obtained from the current sensing device.

8. The method of claim 5, wherein the message is generated upon the occurrence of a trigger event, the trigger event occurring on a periodic basis or on the determination that an amount of recorded electric current values has exceeded a predetermined threshold.

9. An internet-connected server for monitoring an electronic product display device, the internet-connected server comprising:
   an internet connection in communication with the internet;
   a memory that stores data and processor-executable instructions; and
   a processor in communication with the internet connection and the memory, the processor configured to execute the processor-executable instructions to (1) receive, via the internet connection, a message sent from a remote monitoring device over a cellular communication network which is in communication with the internet, the message containing electric current values of the electronic product display device and associated time values, and also containing access point identification information associated with the remote monitoring device, (2) determine the location of the remote monitoring device and the electronic product display device based on the access point identification information, (3) compare the electric current values contained in the received message with at least one electric current threshold to determine whether a usage event has occurred at the electronic product display device from a user interaction with the electronic product display device, and (4) store, in the memory, the location and any determined usage events associated with the electronic product display device.

10. The internet-connected server of claim 9, wherein the determination of whether a usage event has occurred is also based on the time values associated with the electric current values.

11. The internet-connected server of claim 10, wherein the time values associated with the electric current values are compared to at least one timing pattern for the determination of whether a usage event has occurred.

12. The internet-connected server of claim 9, wherein the location of the remote monitoring device and electronic product display device is determined based on the access point identification information by sending the access point identification information to an internet-based location service and receiving location information back from the internet-based location service.

13. A method for monitoring an electronic product display device, the method comprising the steps of:

receiving, via an internet connection, a message sent from a remote monitoring device over a cellular communication network which is in communication with the internet, the message containing electric current values of the electronic product display device and associated time values, and also containing access point identification information associated with the remote monitoring device;

determining the location of the remote monitoring device and the electronic product display device based on the access point identification information;

comparing the electric current values contained in the received message with at least one electric current threshold to determine whether a usage event has occurred at the electronic product display device from a user interaction with the electronic product display device; and storing, in a memory, the location and any determined usage events associated with the electronic product display device.

14. The method of claim 13, wherein the determination of whether a usage event has occurred is also based on the time values associated with the electric current values.

15. The method of claim 14, wherein the time values associated with the electric current values are compared to at least one timing pattern for the determination of whether a usage event has occurred.

16. The method of claim 13, wherein the location of the remote monitoring device and the electronic product display device is determined based on the access point identification information by sending the access point identification information to an internet-based location service and receiving location information back from the internet-based location service.

* * * * *